United States Patent [19]

Johnson et al.

[11] Patent Number: 5,192,757
[45] Date of Patent: * Mar. 9, 1993

[54] COBALT PORPHYRINS

[75] Inventors: Michael R. Johnson, Chapel Hill; Stephen V. Frye, Durham, both of N.C.

[73] Assignee: Glaxo Inc., Research Triangle Park, N.C.

[*] Notice: The portion of the term of this patent subsequent to Sep. 22, 2009 has been disclaimed.

[21] Appl. No.: 631,129

[22] Filed: Dec. 20, 1990

[51] Int. Cl.$^5$ .................. A61K 31/555; C07D 487/22
[52] U.S. Cl. ..................................... 514/185; 540/145
[58] Field of Search ........................ 514/185; 540/145

[56] References Cited

U.S. PATENT DOCUMENTS

| | | | |
|---|---|---|---|
| 4,393,071 | 7/1983 | Fujii et al. | 424/274 |
| 4,619,923 | 10/1986 | Kappas et al. | 514/185 |
| 4,657,902 | 4/1987 | Kappas et al. | 514/185 |
| 4,782,049 | 11/1988 | Kappas et al. | 514/185 |
| 4,948,792 | 8/1990 | Kappas et al. | 514/185 |
| 4,961,920 | 10/1990 | Ward et al. | 424/9 |
| 4,997,828 | 3/1991 | Kappas | 514/185 |
| 5,149,697 | 9/1992 | Johnson | 540/145 |

FOREIGN PATENT DOCUMENTS

| | | | |
|---|---|---|---|
| 188277 | 7/1986 | European Pat. Off. | 514/185 |
| 8704927 | 8/1987 | World Int. Prop. O. | |
| 9009173 | 8/1990 | World Int. Prop. O. | |

OTHER PUBLICATIONS

Ginzburg, Koord. Khim. 3, 77-81 (1977).
Ginzburg Koord. Khim 3, 1779-85 (1977).
Galbraith, J. Steroid Biochem 32, 421 (1989).
Galbraith et al. Proc. Natl. Acad. Sci. USA vol. 86 7653-7657 (1989).
Galbraith et al. Pharmacology 34:241-249 (1987).
Galbraith et al. Neuroendocrinology, 49:641-648 (1989).
Galbraith et al. Biochemical and Biophysical Research Communication. vol. 145, No. 1, 376-383 (1987).
Drummond et al. Proc. Natl. Acad. Sci. USA vol. 79. pp. 2384-2388 (1982).
Smith et al. Pharmacology 34:9-16 (1980).
Smith, "Porphyrins and Metalloporphyrins" (1975) pp. 207-221.
Whitten, J. Org. Chem 28, 2363 (1963).

Primary Examiner—Mark Berch
Attorney, Agent, or Firm—David J. Levy; Charles T. Joyner

[57] ABSTRACT

Cobalt prophyrins of the following formula (I):

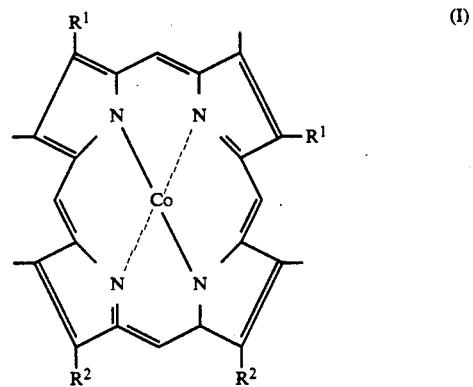

or a salt or ligand complex thereof and their synthesis, pharmaceutical compositions and use in controlling obesity.

14 Claims, No Drawings

COBALT PORPHYRINS

BACKGROUND OF THE INVENTION

Cobalt prophyrins are known to have various endocrine activities including the regulation of food intake for controlling obesity. Publications include those of R. A. Galbraith et al. in Proc. Natl. Acad Sci. USA, vol. 86, pp. 7653-7657 (1989); in Pharmacology 34:241-249 (1987); in Neuroendocrinology 1989, 49:641-648; in Biochemical and Biophysical Research Communications, Vol. 145, No. 1, pp. 376-383 (1987); and those of George S. Drummond et al. in Proc. Natl. Acad. Sci. USA Vol. 79, pp. 2384-2388, April 1982; and Terry J. Smith in Pharmacology, Vol. 34:9, pp. 9-16 (1986).

Phototherapeutic porphyrin-type dimers are disclosed in U.S. Pat. No. 4,961,920. Various porphyrins are disclosed in U.S. Pat. No. 4,393,071 to be useful in treating tumors; in U.S. Pat. No. 4,619,923 to control tryptophan metabolism; in U.S. Pat. No. 4,657,902 to inhibit heme metabolism; and in U.S. Pat. No. 4,782,049 to treat psoriasis. Methods for suppressing the endocrine system with cobalt protoporphyrin are described in U.S. Pat. No. 4,948,792, PCT Patent No. WO 87/04927 and for weight loss in PCT Patent No. WO 90/09173.

SUMMARY OF THE INVENTION

The invention comprises cobalt porphyrins having the following formula (I):

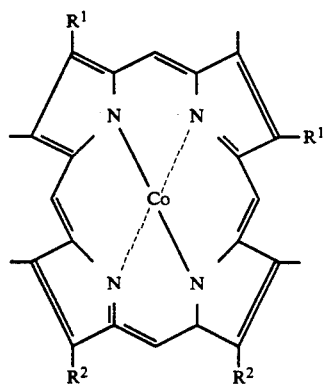

(I)

or a salt or complex thereof with a ligand wherein the cobalt atom is in the +2 or +3 oxidation state, $R^1$ is —$(CH_2)_n$—$X^1$;
n is 0, 1, 2 or 3;
$X^1$ is hydrogen, —COOH, —CONHSO$_2$X$^2$, —CONHCOX$^2$ or tetrazole which is unsubstituted or alkyl-substituted;
$X^2$ is alkyl, phenyl or phenyl independently substituted by one or more of halogen, alkoxy, nitro, alkyl, hydroxy, amino and mono- and di-alkylsubstituted amino; and
$R^2$ is independently a value of $R^1$, provided that i) in one $R^1$ and $R^2$, $X^1$ is other than hydrogen, ii) n is not 0 when $X^1$ is tetrazole and iii) $R^1$ is not H, —CH$_2$CH$_3$ or —CH$_2$CH$_2$COOH when $R^2$ is —CH$_2$CH$_2$COOH.

DETAILED DESCRIPTION OF THE INVENTION

As used herein, halogen includes fluorine, chlorine, bromine and iodine; alkoxy includes those of 1 to 6 carbons such as methoxy, ethoxy and iso-butoxy; and alkyl includes those of 1 to 6 carbons such as methyl, ethyl, sec-pentyl and n-hexyl. Unless otherwise indicated, terms such as alkyl indicate straight or branched configurations; the invention includes all stereoisomers as individual optically active forms as well as racemates; substitution on a ring can be at any position, e.g. o-, m- or p-phenyl for mono-substitution or 3,4 or 3,5 substitution on phenyl for disubstitution; and "independently" indicates that values can be chosen differently among a list when 2 or more are chosen, e.g. $X^2$ can be 3-methyl-4-chlorophenyl.

A particular value of $R^1$ is ethyl and particular values of $R^2$ are $(CH_2)_n$—$X^1$ where n is 2 or 3 and $X^1$ is a tetrazole attached at the 5-position, i.e. at the carbon, for example unsubstituted tetrazole of the formula C(=N=N—N—NH—), —CONHSO$_2$phenyl or —CONHSO$_2$CH$_3$. Particular substituted phenyl values for $X^2$ are 1 or 2 substitutions. The ligands which may attach to the cobalt atom of (I) include aromatic bases such as pyridine, imidazole or 2-methylimidazole in amounts which may be up to 2 equivalents. As a salt of (I), anions may be chloride, bromide, carboxylate or hydroxide. Cations, e.g. when $X^1$ is —COOH are alkali metals such as Na and K.

Particular compounds of formula (I) include the following:
2,4-diethyl-1,3,5,8-tetramethyl-6,7-bis(5-propyl-tetrazole) cobalt porphyrin;
2,4-diethyl-1,3,5,8-tetramethyl-6,7-bis(benzenesulfonyl-propanamide)cobalt porphyrin; or
2,4-diethyl-1,3,5,8-tetramethyl-6,7-bis(methanesulfonyl-propanamide) cobalt porphyrin,
or a salt or complex thereof with a ligand.

SYNTHESIS SCHEMES

Synthetic pathways for the compounds of formula (I) are set forth in the following Schemes with individual steps being the same or analogous to steps taught in the next "Porphyrins and Metalloporphyrins" Ed. by K. M. Smith, Elsevier Scientific Pub. Co (1975) (ISBN 0-444-41375-8). Compounds of the invention wherein $X^1$ is —COOH are described in the Schemes as intermediates for other final products. In the following, the structures of the starting materials and intermediates are defined by the given values of r$^1$ and r$^2$ in the following formula (A):

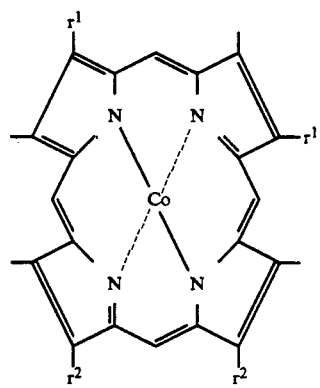

(A)

1. Formula (I) where in $R^1$, n=0 and $X^1$=—COHNSO$_2$X$^2$ or —CONHCOX$^2$, while in $R^2$, n=3 and $X^1$=hydrogen. Begin with protoporphyrin formula (A)

where $r^1$=vinyl and $r^2$=—$(CH_2)_2COOH$) and treat with $LiAlH_4$ in THF to yield (A) where $r^1$=vinyl and $r^2$=—$(CH_2)_2CH_2OH$ which is then treated with $CH_3SO_2Cl$ in THF to produce (A) where $r^1$=vinyl and $r^2$=—$(CH_2)_3OSO_2CH_3$. The products is then reacted with $LiAlH_4$ in THF to yield (A) where $r^1$=vinyl and $r^2$=—$(CH_2)_2CH_3$ which is then oxidized with $KMnO_4$ in acetone to give (A) where $r^1$=—COOH and $r^2$=—$(CH_2)_2CH_3$ which is esterified with p-$NO_2$phenyl-$OCOCF_3$ in pyridine to yield (A) where $r^1$=—COO-phenyl-p-$NO_2$ and $r^2$=—$(CH_2)_3CH_3$. Finally, the product is reacted with a source of —$NHSO_2X^2$ or —$NHCOX^2$ anion, e.g. an amide or sulfonamide with a strong base such as n-butyllithium in an aprotic solvent such as THF, to yield (I) where $R^1$=—$CONHSO_2X^2$ or —$CONHCOX^2$ and $R^2$=—$(CH_2)_2CH_3$.

2. Formula (I) where in $R^1$, n=1 and $X^1$=$CONHSO_2X^2$ or —$CONHCOX^2$ while in $R^2$, n=3 and $X^1$=H. The starting material of formula (A) where $r^1$=vinyl and $r^2$=—$CH_2CH_2CH_3$ is reacted with $Tl(NO_3)$ in methanol followed by $SO_2$ and HCl to yield (A) where $r^1$=—$CH_2CH(OCH_3)_2$ and $r^2$=$CH_2CH_2CH_3$ which is oxidized with $CrO_3$ in $H_2SO_4$ to give (A) where $r^1$=$CH_2COOH$ and $r^2$=—$CH_2CH_2CH_3$. The carboxylic acid is then reacted as in Scheme 1 with $pNO_2$-phenyl$OCOCF_3$ in pyridine to yield (A) where $r^1$=—$CH_2COO$phenyl-$pNO_2$ and $r^2$=$CH_2CH_2CH_3$ which is then reacted with a source of —$NHSO_2X^2$ or —$NHCOX^2$ anion as in Scheme 1 to yield (I) where $R^1$=—$CH_2CONHSO_2X^2$ or —$CHCONHCOX^2$ and $R^2$=—$CH_2CH_2CH_3$.

3. Formula (I) where in $R^1$, n=1 and $X^1$=tetrazole while in $R^2$, n=3 and $X^1$=H. The intermediate (A) of Scheme 1 where $r^1$=COOH and $r^2$=—$CH_2CH_2CH_3$ is reduced with $LiAlH_4$ to yield (A) where $r^1$=—$CH_2OH$ and $r^2$=—$CH_2CH_2CH_3$ which is then reacted with $CH_3SO_2Cl$ to produce (A) where $r^1$=—$CH_2OSO_2CH_3$ and $r^2$=$CH_2CH_2CH_3$. The product is then reacted with NaCN to yield (A) where $r^1$=—$CH_2CN$ and $r^2$=—$CH_2CH_2CH_3$ which is then cyclized with n-$Bu_3SnN_3$ followed by a mineral acid such as HCl or can be cyclized with an alkali metal azide such as $NaN_3$ or $KN_3$ in an aprotic solvent such as THF to yield (I) where $R^1$=—$CH_2C(=N—N=N—NH—)$ and $R^2$=—$CH_2CH_2CH_3$.

4. Formula (I) where in $R^1$, n=2 and $X^1$=—$CONHSO_2X^2$ or —$CONHCOX^2$ while in $R^2$, n=3 and $X^1$=H. The intermediate (A) where $r^1$=—$CH_2CH(OCH_3)_2$ and $r^2$=—$CH_2CH_2CH_3$ from Scheme 2 is reduced with $LiAlH_4$ to yield (A) where $r^1$=$CH_2CH_2OH$ and $r^2$=—$CH_2CH_2CH_3$ which can then be reacted with $CH_3SO_2Cl$ to give (A) where $r^1$=—$CH_2CH_2OSO_2CH_3$ and $r^2$=—$CH_2CH_2CH_3$ which is reacted with NaCN to yield (A) where $r^1$=—$CH_2CH_2CN$ and $r^2$=—$CH_2CH_2CH_3$. The product is then reacted with $CH_3OH$ and HCl followed by KOH in $H_2O$ to give (A) where $r^1$=—$CH_2CH_2COOH$ and $r^2$=—$CH_2CH_2CH_3$. This product is then reacted with p-$NO_2$phenyl-$OCOCF_3$ in pyridine to give (A) where $r^1$=$CH_2CH_2COO$phenyl-p-$NO_2$ and $r^2$=$CH_2CH_2CH_3$ which is then reacted with a source of —$NHSO_2X^2$ or —$NHCOX^2$ anion as in Scheme 1 to yield (I) where $R^1$=—$CH_2CH_2CONHSO_2X^2$ or —$CH_2CH_2CONHCOX^2$ and $R^2$=$CH_2CH_2CH_3$.

5. Formula (I) where in $R^1$, n=2 and $X^1$ is unsubstituted tetrazole while in $R^2$, n=3 and $X^1$=H. The intermediate (A) where $r^1$=—$CH_2CH_2CN$ and $r^2$=—$CH_2CH_2CH_3$ from Scheme 4 is reacted with n-$Bu_3SnN_3$ or as described in Scheme 3 followed by HCl to yield the title product.

6. Formula (I) where in $R^1$, n=3 and X=—$NHSO_2X^2$ or —$NHCOX^2$ while in $R^2$, n=3 and $X^1$=H. The intermediate (A) where $r^1$=—$CH_2CH_2OSO_2CH_3$ and $r^2$=—$CH_2CH_2CH_3$ is reacted with a source of —$CH(COOOCH_3)_2$ anion such as dimethylmalonate and sodium hydride followed by heating with HCl to yield (A) where $r^1$=—$(CH_2)_3COOH$ and $r^2$=—$CH_2CH_2CH_3$ which is then esterified with p-$NO_2$phenyl-$OCOCF_3$ in pyridine to produce (A) where $r^1$=—$(CH_2)_3COO$phenyl-p-$NO_2$ and $r^2$=—$CH_2CH_2CH_3$. The product is then reacted with a source of —$NHSO_2X^2$ or —$NHCOX^2$ anion as in Scheme 1 to yield the title product.

7. Formula (I) wherein $R^1$, n=3 and $X^1$ is unsubstituted tetrazole while in $R^2$, n=3 and $X^1$=H. The intermediate of formula (A) where $r^1$=—$CH_2CH_2COOH$ and $r^2$=—$CH_2CH_2CH_3$ from Scheme 4 is reduced with $LiALH_4$ to (A) where $r^1$=$(CH_2)_3OH$ and $r^2$=—$CH_2CH_2CH_3$ which is then reacted with $CH_3SO_2Cl$ to give (A) where $r^1$=—$(CH_2)_3OSO_2CH_3$ and $r^2$=—$CH_2CH_2CH_3$. This product is then reacted with KCNNaCN to give (A) where $r^1$=—$(CH_2)_3CN$ and $r^2$=—$CH_2CH_2CH_3$ which may then be reacted with n-$Bu_3SnN_3$ and then HCl or as described in Scheme 3 to give the title product.

8. Formula (I) wherein $R^1$, n=2 and $X^1$=H, while in $R^2$, n=0 and $X^1$=—$CONHSO_2X^2$ or —$CONHCOX^2$. Mesoporphyrin of the formula (A) where $r^1$=—$CH_2CH_3$ and $r^2$=—$CH_2CH_2COOCH_3$ is reacted with 2 equivalents of phenylmagnesium bromide followed by heat to yield (A) where $r^1$=—$CH_2CH_3$ and $r^2$=—$CH_2CH=CPh_2$ which is oxidized with $NaIO_4$ and $RuO_4$ to produce (A) where $r^1$=—$CH_2CH_3$ and $r^2$=—$CH_2COOH$. This product is then esterified with $CH_3OH$ and $H_2SO_4$ to (A) where $r^1$=—$CH_2CH_3$ and $r^2$=—$CH_2COOCH_3$ whereupon the same sequence is repeated by reaction with PhMgBr and heated to yield (A) where $r^1$=—$CH_2CH_3$ and $r^2$=—$CH=CPh_2$. This product is reacted with $NaIO_4$ and $RuO_4$ to give (A) where $r^1$=—$CH_2CH_3$ and $r^2$=—COOH which is then reacted with $pNO_2$phenyl-$OCOCF_3$ as in Schemes 4 and 6 to produce (A) where $r^1$=—$CH_2CH_3$ and $r^2$=—$COO$phenyl-p-$NO_2$. This product can then be reacted with a source of —$NHSO_2X^2$ or —$NHCOX^2$ anion as in Scheme 1 to yield the title product.

9. Formula (I) where in $R^1$, n=2 and $X^1$=H while in $R^2$, n=1 and $X^1$=—$CONHSO_2X^2$ or —$CONHCOX^2$. The intermediate from Scheme 8 of formula (A) where $r^1$=—$CH_2CH_3$ and $r^2$=—$CH_2COOH$ is reacted with $pNO_2$-phenyl-$OCOCF_3$ to give (A) where $r^1$=$CH_2CH_3$ and $r^2$=—$CH_2 CH_2COO$phenyl-$pNO_2$. This product can then be reacted with a source of —$NHSO_2X^2$ or —$NHCOX^2$ anion as in Scheme 1 to yield the title product.

10. Formula (I) wherein $R^1$, n=2 and $X^1$=H while in $R^2$, n=3 and $X^1$=—$CONHSO_2X^2$ or —$CONHCOX^2$. Sodium cyanide is reacted with 2,4-diethyl-1,3,5,8-tetramethyl-6,7-bis-(3-methylsulphonylpropyl)porphyrin as in Example 1 to yield the compound of formula (IIIa), i.e. (A) where $r^1$=$CH_2CH_3$ and $r^2$=$CH_2CH_2CN$. This product is then reacted with $CH_3OH$ and $H_2SO_4$ followed by KOH in THF to yield (A) where $r^1$=$CH_2CH_3$ and $r^2$=—$(CH_2)_3COOH$ which is then reacted with p-$NO_2$phenyl-$OCOCF_3$ to give (A) where $r^1$=—$CH_2CH_3$ and $r^2$=—$(CH_2)_3$—COO phenyl-$NO_2$. This product is then reacted with a source of —NHSO$_2$X$^2$ or —NHCOX$^2$ anion as in Scheme 1 to yield the title product.

11. Formula (I) wherein in R$^1$, n=2 and X$^1$=H while in R$^2$, n=1 and X$^1$=unsubstituted tetrazole. The intermediate (A) from Scheme 8 where r$^1$=—CH$_2$CH$_3$ and r$^2$=—COOH is reduced with LiALH$_4$ to yield (A) where r$^1$=—CH$_2$CH$_3$ and r$^2$=—CH$_2$OH which is then reacted with CH$_3$SO$_2$Cl to give (A) where r$^1$=—CH$_2$CH$_3$ and r$^2$=—CH$_2$OSO$_2$CH$_3$. This intermediate is then reacted with NaCN as in Example 1 to produce (A) where r$^1$=—CH$_2$CH$_3$ and r$^2$=—CH$_2$CN. Finally, this product is reacted with n-Bu$_3$SnN$_3$ or as described in Scheme 3 followed by HCl to yield the title product.

12. Formula (I) where in R$^1$, n=2 and X$^1$=H while in R$^2$, n=2 and X$^1$=unsubstituted tetrazole. The intermediate (A) of Scheme 8 where r$^1$=—CH$_2$CH$_3$ and r$^2$=—CH$_2$COOH is reduced with LiAIH$_4$ to give (A) where r$^1$=—CH$_2$CH$_3$ and r$^2$=CH$_2$CH$_2$OH which is then reacted with CH$_3$SO$_2$Cl to yield (A) where r$^1$=—CH$_2$CH$_3$ and r$^2$=—CH$_2$CH$_2$OSO$_2$CH$_3$. This intermediate is reacted with NaCN to give (A) when r$^1$=—CH$_2$CH$_3$ and r$^2$=—CH$_2$CH$_2$CN which may be reacted with n-BuSnN$_3$ or as described in Scheme 3 followed by HCl to produce the title product.

13. Formula (I) which is a complex formed with a ligand. A compound of formula (A) where r$^1$ and r$^2$ are as defined for R$^1$ and R$^2$ in formula (I) is complexed with an aromatic base such as 2-methylimidazole or pyridine in THF at temperature of about 25° to 95° C.

14. Formula (I) where in R$^1$ or R$^2$, X$^1$ is an alkyl-substituted tetrazole. Reaction of a compound of formula (A) where one of r$^1$ and r$^2$ is —CH$_2$X$^3$, —CH$_2$CH$_2$X$^3$ or —CH$_2$CH$_2$CH$_2$X$^3$ and X$^3$ is unsubstituted tetrazole of the formula —C(=N—N=N—NH—) with K$_2$CO$_3$ in the presence of an alkylhalide yields the title product.

PHARMACOLOGY

Measurement of the effects of cobalt porphyrins on food intake, body weight and serum hormone concentration can be carried out according to the following protocol:

Male Long-Evans rats (Charles River, Raleigh, NC), weighting between 250–325 grams, were used to measure the effects of subcutaneous (s.c) administration of CoMP (cobalt mesoporphyrin), control (0.5% methylcellulose or 0.9% NaCl; 2 ml/kg) and the porphyrins of the invention on food intake, body weight (B.W.) and serum concentrations of T$_3$, T$_4$ and testosterone. The analogues were measured in one of four test groups. Each test group always contained a group receiving 50 mm/kg CoMP as well as a control group. All cobalt porphyrins were ground with a mortar and pestle, weighed, suspended in 0.5% methylcellulose, and administered s.c. at 50 mm/kg B.W. Solid food (Lab Blox, Purina Rodent Laboratory Chow #5001) intake (to the enarest 0.1 g) and B.W. (to the nearest g) were measured before drug administration and on days 1, 3, 7, 14 and 21 following drug administration, and compared with values from appropriate control-treated rats with the 2-tailed t-test for independent samples. Either on days 3 or day 22 following drug administration rats were guillotined, their blood was collected and centrifuged, and collected serum was frozen in triplicate at −70° C. Subsequently, serum samples were assayed to T$_3$, T$_4$ or testosterone by radioimmunoassay, and values of test compound groups were compared with appropriate control groups with the 2-tailed-t-test for independent samples.

The methods of the invention are useful for the treatment of diabetes mellitus, Type II, the so called adult type. This type of diabetes is normally treated by diet control. For this utility, the two pronged attack of appetite suppression coupled with actual weight loss is ideal.

PHARMACEUTICAL COMPOSITIONS

Also parts of the present invention are pharmaceutical compositions containing compounds of formula (I) in combination with a pharmaceutically acceptable diluent or carrier as well as methods for treating obesity in an obese patient or treating diabetes which involves administering such a pharmaceutical composition to the patient.

The compounds of the invention of formula (I) are useful in treating man and animals, particularly pets such as cats and dogs, and domesticated farm animals such as pigs.

The compounds of the invention of formula (I) can be administered orally, topically or parenterally, e.g. rectal or i.v., of which the preferred route is parenterally. The compounds may be admixed with conventional tableting aids, diluents, excepients as known in the art to form tablets, capsules, powders, elixirs, liquids or suspensions as known in the pharmaceutical art. For administration to humans, the compounds of the invention may be administered in an amount of about 0.1 to 1.0 mm/kg about 1–4 times per day. The particular dosage will depend on the activity of the specific compound chosen and the severity of the physiological condition being treated. The projected dosage can be determined by correlation of test results in pharmacological tests for known anti-obesity agents such as cobalt protoporphyrin and cobalt mesoporphyrin as described in PCT Patent WO 90/09173 to those for compounds of formula (I).

In more detail, the compounds of the invention will normally be administered parenterally, i.e. intravenously, subcutaneously or intramuscularly in sterile, isotonic parenteral solutions. For such solutions, any of a wide variety of pharmaceutically acceptable carriers currently in use for the preparation of parenteral solutions may be employed. The solutions may be buffered, for example with a phosphate buffer to a pH of about 7 to 8, preferably 7.4 to 7.5, and contain such solutes as saline or glucose. The solutions may also contain a polyhydroxy alcohols such as ethylene or propylene glycol. The active compounds may also be administered in solution or suspension in a sterile inert oil such as sesame or safflower oil. A typical dosage regimen for humans will be from about 0.5 to 2 mm/kg b.w. per week.

Typically, isotonic solutions for use in this invention can be prepared by dissolving the selected amount of active compound in 0.1M aqueous sodium hydroxide solution, adjusting to the selected pH with 1M hydrochloric acid, and making up to volume with 0.9 aqueous sodium chloride solution. For the low levels of active agent utilized in the practice of this invention, parenteral compositions will normally be prepared to contain from about 1 to 15 mg/ml.

The physician or veterinarian will determine the specific dosage, and it will depend upon such well understood factors as the age, weight and general health of the patient. Typically, treatment will be initiated at a dosage level of about 0.5 to 1 mm/kg b.w. and the patient will be observed so that the decline in weight is not too precipitious. Too rapid a decline in weight could elicit toxic effects similar to those observed in starvation, i.e., kidney damage, ketosis, electrolyte imbalance, etc. Therefore, the object will be to decrease weight gradually, in effect to titrate the patient so that the weight is brought under control without attendant undesirable effects.

INTERMEDIATES

Also part of the present invention are novel intermediates, e.g. of the following formulae (III) and (IV):

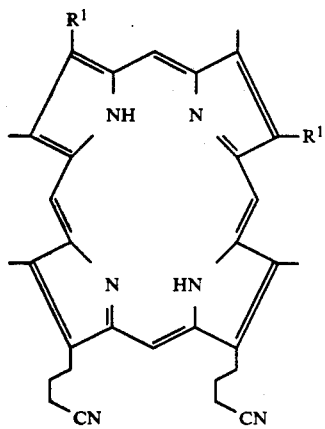
(III)

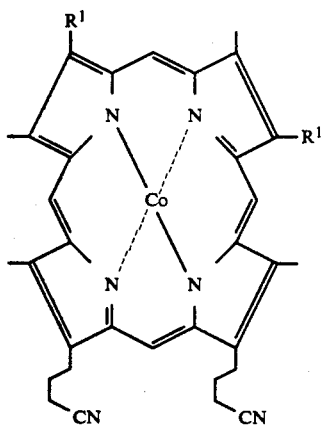
(IV)

where $R^1$, n, $X^1$ and $X^2$ are as defined for formula (I), e.g. of the formula (IV) where $R^1$=ethyl. Another such intermediate which is part of the invention is that of the following formula (IV):

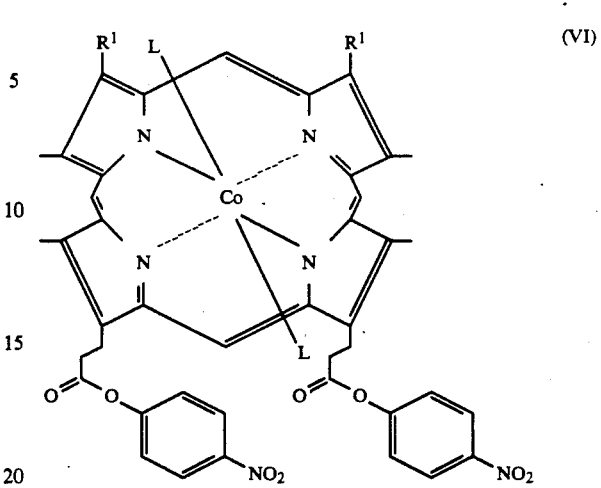
(VI)

where $R^1$, n, $X^1$ and $X^2$ are as defined for formula (I), e.g. where $R^1$=ethyl and two equivalents of pyridine are attached as ligands.

In the following Examples and throughout the specification, the following abbreviations may be used: g (grams); ml (milliliters); hrs (hours); TLC (thin layer chromatography); >(greater than); m.p. (melting point); uv (ultraviolet); Me (methyl); THF (tetrahydrofuran); LiAlH$_4$ (lithium aluminum hydride); CH$_3$SO$_2$Cl (methanesulfonyl chloride); ppm (parts per million); mmol (millimoles); py (pyridine); kg b.w. (kilograms of body weight); and mm (micromoles). Unless otherwise noted, all temperatures are in ° C. (degrees Centigrade).

EXAMPLES

EXAMPLE 1

(Formula IIIa)

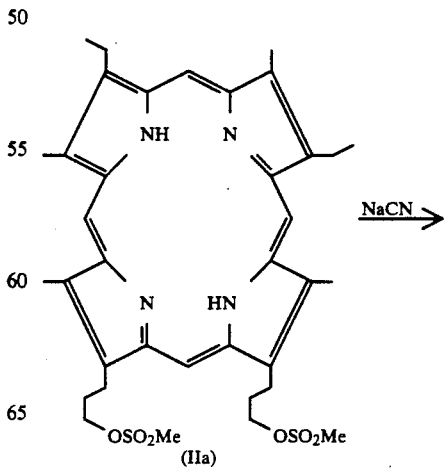
(IIa)

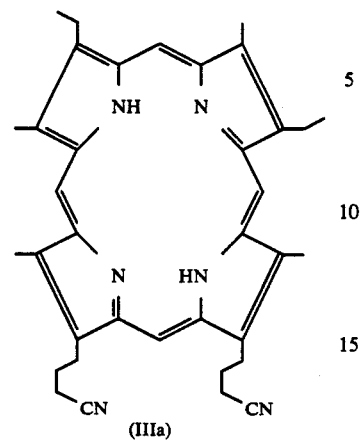

(IIIa)

To a mixture of 2,4-diethyl-1,3,5,8-tetramethyl-6,7-bis-(3-methylsulphonylpropyl)porphyrin (prepared according to Burns, D. H., et al., J. Chem. Soc. Perkin Trans. 1, 1988, 3119) (1.66 g, 2.4 mmol) and sodium cyanide (1.71 g, 24 mmol) is added dimethyl sulfoxide (25 ml) and the solution heated at 50° C. for 8 hrs. The reaction is then poured into a mixture of chloroform (100 ml) and saturated aqueous sodium chloride (50 ml), the layers separated and the chloroform layer washed with water (2×30 ml), dried over sodium sulfate, concentrated and purified by flash chromatography on silica gel (1% methanol, 99% chloroform mobile phase) to give 2,4-diethyl-1,3,5,8-tetramethyl-6,7-bis(butanenitrile)-porphyrin; yield: 0.99 g (75%); m.p.>250° C.; pure by TLC 1% CH$_3$OH, 99% chloroform) on silica gel.

| Elemental Analysis for C$_{36}$H$_{40}$N$_6$.H$_2$O: | | | |
|---|---|---|---|
| | % C | % H | % N |
| Calculated: | 75.23 | 7.37 | 14.62 |
| Found: | 75.52 | 7.10 | 14.64 |

FAB mass spectrum in meta-nitrobenzyl alcohol; m/z 557 (mH+)

EXAMPLE 2

2,4-Diethyl-1,3,5,8-tetramethyl-6,7-bis(butanenitrile) cobalt porphyrin (Formula (I): (IVa))

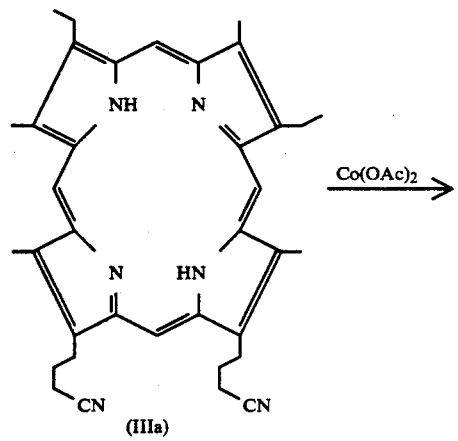

(IIIa) →[Co(OAc)$_2$]

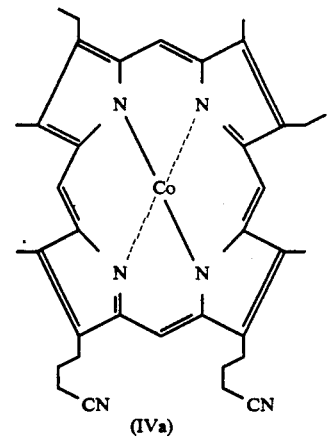

(IVa)

To a solution of 2,4-diethyl-1,3,5,8-tetramethyl-6,7-bis(butanenitrile)porphyrin (2.47 g, 4.4 mmol obtained in Example 1 in chloroform (350 ml) is added cobalt acetate tetrahydrate (1.65 g, 6.6 mmol) in methanol for 2 hrs with a drying tube attached. The solution is then filtered through silica gel and concentrated to give the title product; yield; 2.54 g (94%); m.p. 237°–240° C.; pure by TLC (1% MeOH, 99% chloroform) on silica gel.

| Elemental Analysis for C$_{36}$H$_{38}$N$_6$Co.$\frac{1}{2}$H$_2$O) | | | |
|---|---|---|---|
| | % C | % H | % N |
| Calculated: | 69.44 | 6.31 | 13.49 |
| Found: | 69.87 | 6.31 | 13.58 |

FAB mass spectrum in meta-nitrobenzyl alcohol: m/z 613 (M+).

EXAMPLE 3

2,4-Diethyl-1,3,5,8-tetramethyl-6,7-bis(5-propyltetrazole)cobaltporphyrinchloride (Formula (I):R$^2$=—CH$_2$CH$_2$CH$_2$-5-tetrazole))

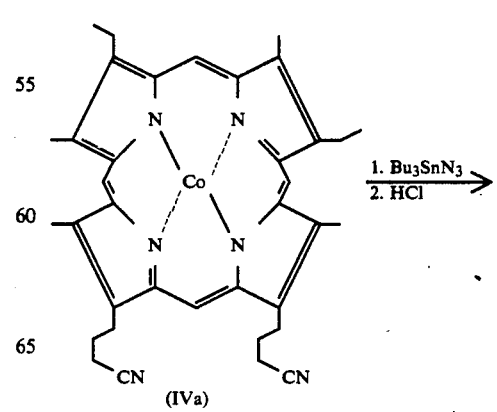

(IVa) →[1. Bu$_3$SnN$_3$ / 2. HCl]

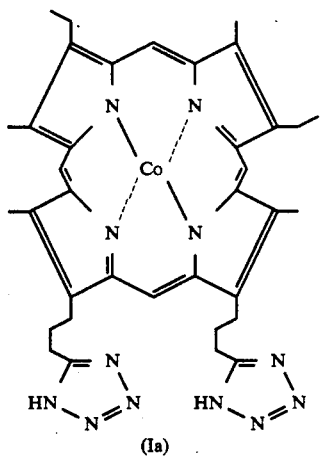

(Ia)

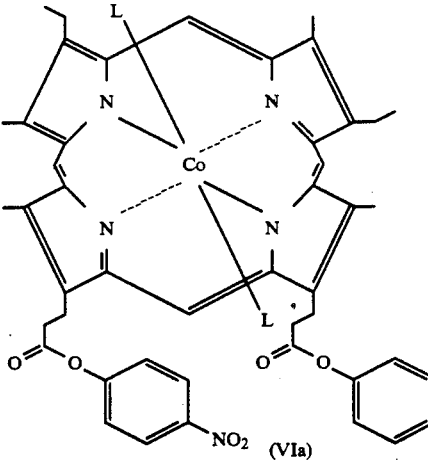

(VIa)

To 2,4-diethyl-1,3,5,8-tetramethyl-6,7-bis-(butanenitrile) cobalt porphyrin (1.00 g, 1.63 mmol) is added freshly distilled tributyltinazide (15 ml) and the mixture is heated at 100° C. overnight under argon with vigorous mechanical stirring. The excess tributyltin azide is then removed by distillation and the resulting solid treated with diethyl ether (50 ml) saturated with hydrochloric acid for one hr. The solid is then collected by filtration and washed extensively with diethyl ether to give the 2,4-diethyl-1,3,5,8-tetramethyl-6,7-bis-(5-propyltetrazole) cobalt porphyrin chloride; yield: 0.865 g (75%); m.p.>250° C.; >99% purity by UV at 415 nm reverse phase HPLC (C-8 column, 20:80 solvent A to B; solvent A-60:40 methanol; 1M ammonium acetate; solvent B-90:10 methanol: 1M ammonium acetate).

To a solution of cobalt mesoporphyrin (3.62 g, 5.81 mmol in dry pyridine (200 ml) is added para-nitrophenyl trifluoroacetate (4.73 g, 20 mmol) and the reaction is allowed to stir overnight under nitrogen. The solution is then concentrated to a solid and purified by flash chromatography on silica gel (15–20% methanol, 85–80% chloroform) to give 2,4-diethyl-1,3,5,8-tetramethyl-6,7-bis(paranitrophenyl propionate)bispyridinecobalt porphyrin; yield: 4.57 g (77%); m.p. 83°–90° C., which was of sufficient purity to carry on to Example 5.

FAB mass spectrum in meta nitrobenzyl alcohol: m/z 865 (M+ −2py).

EXAMPLE 5

2,4-Diethyl-1,3,5,8-tetramethyl-6,7-bis(benzenesulfonylpropanamide)-bispyridine cobaltporphyrin (Formula (I): $R^2 = CH_2CONHSO_2phenyl$))

| Elemental Analysis for $C_{36}H_{40}N_{12}CoCl$: | | | |
|---|---|---|---|
| | % C | % H | % N |
| Calculated: | 58.82 | 5.48 | 22.86 |
| Found: | 58.74 | 5.67 | 22.66 |

High-resolution mass spectrum calculated for $C_{36}H_{40}N_{12}Co$ 699.2830; found: 699.2881, error 7.3 ppm.

EXAMPLE 4

2,4-Diethyl-1,3,5,8-tetramethyl-6,7-bis(paranitrophenylpropionate)-bispyridine cobaltporphyrin (VIa) 

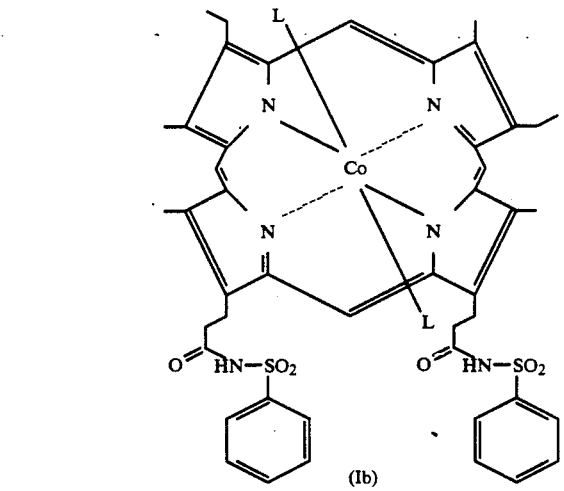

(Ib)

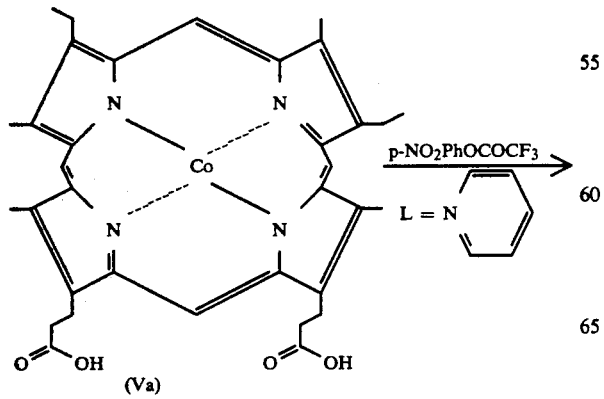

(Va)

To a solution of freshly sublimed benzenesulfonamide (0.348 g, 2.2 mmol) in tetrahydrofuran (30 ml) at 0° C. under argon is added n-butyllithium (1.37 ml, 1.6 M in hexanes, 2.2 mmol) and the resulting slurry is stirred for 10 min before a solution of 2,4-diethyl-1,3,5,8-tetramethyl-6,7-bis(paranitrophenylpropionate)-bispyridine-cobalt porphyrin (750 g, 0.73 mmol) in tetrahydrofuran (75 ml) is added dropwise. After one hr at 0° C. the solution is concentrated, the residue dissolved in chloroform (150 ml), washed with water (2×100 ml), dried over sodium sulfate, concentrated and purified by flash chromatography on silica gel (5% methanol, 95% chloroform) to yield the title product; yield: 0.284 g (38%); m.p. 133°–137° C.; pure by TLC (5% methanol, 95% chloroform) on silica gel.

High-resolution mass spectrum: calculated for $C_{46}H_{46}N_6O_6S_2Co$: 901,2250; found: 901.2255; error 0.6 ppm.

EXAMPLE 6

2,4-diethyl-1,3,5,8-tetramethyl-6,7-bis-(methanesulfonylpropanamide)-bispyridine cobaltporphyrin (Formula (I): $R^2 = -CH_2CONHSO_2CH_3$)

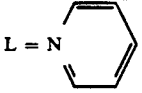

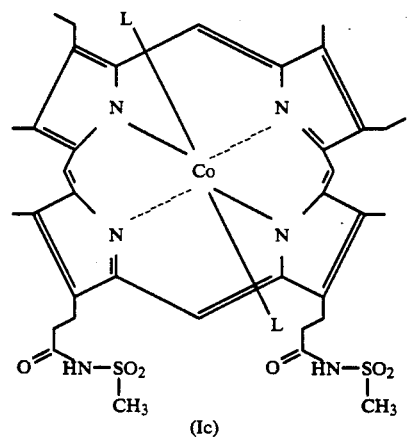

(Ic)

The procedure of Example 5 was followed except methane sulfonamide was substituted for benzone sulfonamide to 2,4-diethyl-1,3,5,8-tetramethyl-6,7-bis (methanesulfonyl-propanamide) bispyridinecobalt porphyrin, yield: (67%); m.p. >250° C. pure by TLC (5% methanol, 95% chloroform) on silica gel.

High-resolution mass spectrum: calculated for $C_{36}H_{42}N_6O_6S_2Co$: 777.1938; found: 777.1961, error 3.0 ppm.

EXAMPLE 7-11

In a manner similar to the previous examples or as described in the Synthesis Schemes, the following compounds of the invention may be prepared:

TABLE 1

| Example | Formula (I) $R^1$ | $R^2$ |
|---|---|---|
| 7 | $-CH_2CH_2CONHSO_2CH_3$ | $-CH_2CH_3$ |
| 8 | $-CH_2CONHCOC_6H_5$ | $-H$ |
| 9 | $-CH_2CONHCOCH_3$ | $-CH_2CONHCOCH_3$ |
| 10 | $-CONHSO_2CH_3$ | $-CONHCOC_6H_5$ |

TABLE 1-continued

| Example | Formula (I) $R^1$ | $R^2$ |
|---|---|---|
| 11 | $-CH_2CH_2CH_2CH_3$ | $-CH_2CH_2CH_2$tetrazole |

EXAMPLE A

The following examples illustrate pharmaceutical formulations according to the invention containing 2,4-diethyl-1,3,5,8-tetramethyl-6,7-bis(5-propyltetrazole) cobaltporphyrinchloride as the active ingredient. Other compounds of the invention may be formulated in a similar manner.

| TABLETS FOR ORAL ADMINISTRATION DIRECT COMPRESSION | mg/tablet |
|---|---|
| Active Ingredient | 25 |
| Calcium hydrogen phosphate B.P.* | 72.5 |
| Croscarmellose sodium USP | 2.00 |
| Magnesium Stearate, B.P. | 0.50 |
| Compression Weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machined fitted with 5.5 mm flat bevelled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| CAPSULES | mg/tablet |
|---|---|
| Active Ingredient | 25 |
| *Starch 1500 | 174 |
| Magnesium Stearate | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| SYRUP | mg/5 ml dose |
|---|---|
| Active Ingredient | 25 |
| Buffer | as required |
| Flavour | as required |
| Colour | as required |
| Preservative | as required |
| Thickening Agent | as required |
| Sweetening agent | as required |

-continued

| SYRUP | |
|---|---|
| | mg/5 ml dose |
| Purified Water to | 5.00 ml |

The active ingredient, buffer, flavour, colour, preservative, thickening agent and sweetening agent are dissolved in some water, the solution is adjusted to volume and mixed. The syrup produced is clarified by filtration.

What is claimed is:

1. A cobalt porphyrin of the following formula (I):

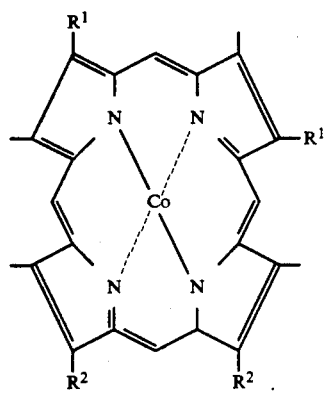
(I)

or a salt or complex thereof with a ligand wherein the cobalt atom is in the +2 oxidation state, wherein said ligand is up to 2 molecules of an aromatic base selected from the group consisting of pyridine, imidazole or 2-methyl-imidazole and wherein:

$R^1$ is —$(CH_2)_n$—$X^1$;

n is 0, 1, 2 or 3;

$X^1$ is hydrogen, —COOH, —CONHSO$_2$X$^2$, —CONHCOX$^2$ or tetrazole which is unsubstituted or alkyl-substituted;

$X^2$ is alkyl, phenyl or phenyl independently substituted by one or more of halogen, alkoxy, nitro, alkyl, hydroxy, amino and mono- and dialkyl substituted amino;

$R^2$ is independently a value of $R^1$, provided that i) in one of $R^1$ and $R^2$, $X^1$ is other than hydrogen, ii) n is not 0 when $X^1$ is tetrazole and iii) $R^1$ is not H, —$CH_2CH_3$ or —$CH_2CH_2COOH$ when $R^2$ is —$CH_2CH_2COOH$.

2. The porphyrin of claim 1, wherein $R^1$ is ethyl.

3. A pharmaceutical composition which comprises a porphyrin of claim 1 in combination with a pharmaceutically acceptable diluent or carrier.

4. A method for treating obesity in an obese patient or animal which comprises administering to said patient or animal, an effective obesity treating amount of the pharmaceutical composition of claim 3.

5. The porphyrin of claim 1 wherein said $R^2$ is —$(CH_2)_nX^1$ and $X^1$ is —CONHSO$_2$X$^2$ or unsubstituted tetrazole.

6. The porphyrin of claim 1, wherein said porphyrin is in the form of a complex with a ligand.

7. A porphyrin of the following formula (VI):

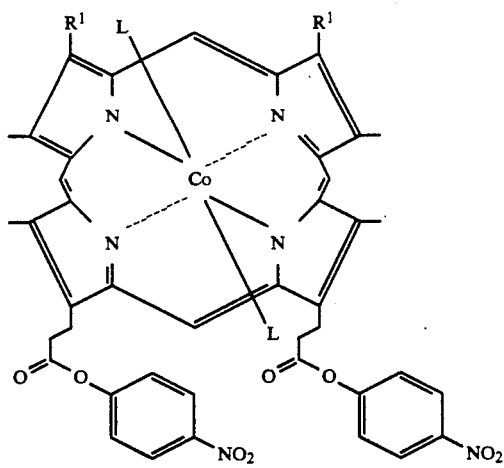
(VI)

or a salt thereof wherein the cobalt atom is in the +2 oxidation state, wherein $R^1$ is —$(CH_2)n$-$X^1$;

n is 0, 1, 2 or 3;

$X^1$ is hydrogen, —COOH, —CONHSO$_2$X$^2$, —CONHCOX$^2$ or tetrazole which is unsubstituted or alkyl-substituted;

$X^2$ is alkyl, phenyl or phenyl independently substituted by one or more of halogen, alkoxy, nitro, alkyl, hydroxy, amino and mono-and di-alkyl substituted amino; and L is a ligand of up to 2 molecules of an aromatic base selected from the group consisting of pyridine, imidazole or 2-methyl-imidazole, provided that n is not 0 $X^1$ is tetrazole.

8. The porphyrin of claim 7, wherein said porphyrin of formula (VI) is of the following formula (VIa):

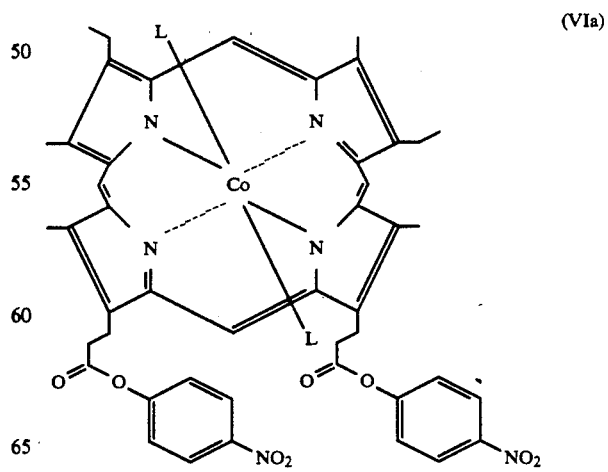
(VIa)

9. A porphyrin of the following formula (IV):

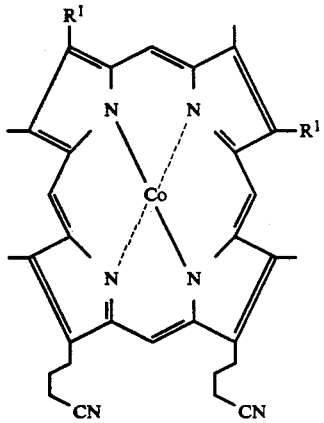

(IV)

or a salt or complex thereof with a ligand wherein the cobalt atom is in the +2 oxidation state, wherein said ligand is up to 2 molecules of an aromatic base selected from the group consisting of pyridine, imidazole or 2-methyl-imidazole and wherein:

$R^1$ is $-(CH_2)_n-X^1$;

n is 0, 1, 2 or 3;

$X^1$ is hydrogen, $-COOH$, $-CONHSO_2X^2$, $-CONHCOX^2$ or tetrazole which is unsubstituted or alkyl-substituted; and $X^2$ is alkyl, phenyl or phenyl independently substituted by one or more of halogen, alkoxy, nitro, alkyl, hydroxy, amino and mono- and di-alkyl substituted amino, provided that n is not 0 when $X^1$ is tetrazole.

10. The porphyrin of claim 1, wherein $R^1$ is ethyl and in $R^2$, n is 1.

11. The porphyrin of claim 1, wherein $R^2$ is ethyl and in $R^2$, n is 2.

12. The porphyrin of claim 1, wherein $R^1$ is ethyl and in $R^2$, n is 3.

13. The porphyrin of claim 1, wherein said porphyrin is selected from the group consisting of:
2,4-diethyl-1,3,5,8-tetramethyl-6,7-bis(5-propyl-tetrazole) cobaltporphyrin;
2,4-diethyl-1,3,5,8-tetramethyl-6,7-bis(benzenesulfonyl propanamide) cobalt porphyrin; or
2,4-diethyl-1,3,5,8-tetramethyl-6,7-bis(methanesulfonyl propanamide) cobalt porphyrin,
or a salt or complex thereof with a ligand.

14. The porphyrin of claim 9, wherein said porphyrin of formula (IV) is of the following formula (IVa):

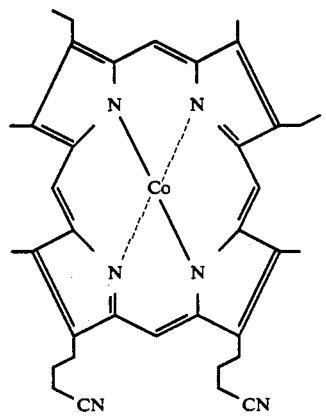

(IVa)

* * * * *